(12) United States Patent
Zhu et al.

(10) Patent No.: US 10,464,882 B2
(45) Date of Patent: Nov. 5, 2019

(54) Y-TYPE DISCRETE POLYETHYLENE GLYCOL DERIVATIVE AND PREPARATION METHOD THEREOF

(71) Applicant: JENKEM TECHNOLOGY CO., LTD. (BEIJING), Beijing (CN)

(72) Inventors: Hui Zhu, Beijing (CN); Meina Lin, Beijing (CN); Xiaomeng Chen, Beijing (CN); Zhen'gang Zhu, Beijing (CN); Xuan Zhao, Beijing (CN)

(73) Assignee: JENKEM TECHNOLOGY CO., LTD. (BEIJING), Beijing (CN)

( * ) Notice: Subject to any disclaimer, the term of this patent is extended or adjusted under 35 U.S.C. 154(b) by 0 days.

(21) Appl. No.: 15/791,405

(22) Filed: Oct. 23, 2017

(65) Prior Publication Data

US 2018/0044280 A1    Feb. 15, 2018

Related U.S. Application Data

(63) Continuation of application No. PCT/CN2016/079747, filed on Apr. 20, 2016.

(30) Foreign Application Priority Data

Apr. 24, 2015   (CN) .......................... 2015 1 0202435

(51) Int. Cl.
| | |
|---|---|
| *C07C 217/28* | (2006.01) |
| *C07C 213/06* | (2006.01) |
| *C08G 65/26* | (2006.01) |

(52) U.S. Cl.
CPC .......... *C07C 217/28* (2013.01); *C07C 213/06* (2013.01); *C08G 65/2618* (2013.01); *C08G 2650/30* (2013.01); *C08G 2650/50* (2013.01)

(58) Field of Classification Search
CPC combination set(s) only.
See application file for complete search history.

(56) References Cited

U.S. PATENT DOCUMENTS

2011/0243892 A1* 10/2011 Ji .......................... C08G 65/329
424/85.5

FOREIGN PATENT DOCUMENTS

GB           897163       *  5/1962

OTHER PUBLICATIONS

Snider et al. J. of Chromat. A, 1992, 599 141-155.*

* cited by examiner

*Primary Examiner* — Ana Z Muresan
(74) *Attorney, Agent, or Firm* — Flener IP & Business Law; Zareefa B. Flener

(57) ABSTRACT

The present invention discloses a Y-type discrete polyethylene glycol derivative, which has the advantages of determined molecular weights and the number of chain segments, and can avoid the defect of heterogeneity of a PEG derivative. In addition, the Y-type discrete polyethylene glycol derivative of the present invention may increase the water solubility of the discrete polyethylene glycol, and solve the problem of insufficient water solubility of the discrete polyethylene glycol-modified insoluble drug caused by an increase of the loading capacity.

11 Claims, 3 Drawing Sheets

Y-TYPE DISCRETE POLYETHYLENE GLYCOL DERIVATIVE AND PREPARATION METHOD THEREOF

CROSS-REFERENCE TO RELATED APPLICATION

This application is a continuation application of International patent application No. PCT/CN2016/079747, filed on Apr. 20, 2016, which claims the benefit and priority of Chinese patent application No. CN201510202435.9, filed on Apr. 24, 2015, each of which is incorporated herein by reference in its entirety and for all purposes.

FIELD OF THE INVENTION

The present invention relates to a Y-type discrete polyethylene glycol derivative and a preparation method thereof, in particular, the present invention relates to a discrete polyethylene glycol derivative having a branched structure with N as a branch node.

BACKGROUND OF THE INVENTION

Polyethylene glycol (PEG) is considered to be the polymer with the lowest level of protein and cell absorption in known polymers, and it has advantages of good water solubility and biocompatibility, no toxicity, no immunity, no teratogenicity and no antigenicity, and is widely used in drug modification, agent preparation and medical materials and other fields. Since 1991, after the first PEG-modified drug PEG-ADA was approved by the FDA, the major pharmaceutical companies have put a great interest in research and development of PEG in the field of drug. In recent years, the products on the market include PEG-somatostatin, PEG-interferon, PEG-granulocyte colony stimulating factor, etc. At present, there are further dozens of PEG-modified drugs which are in the process of research or clinical trial.

Although PEG has a unique advantage in the field of drug modification, it has some shortcomings: 1) PEG is a polymer product, which is a mixture that has a defect of heterogeneity in itself, which may not only limit the use of PEG, e.g., when PEG is used to modify the superoxide dismutase, a series of heterogeneous products may be produced (Characterization of the heterogeneity of polyethylene glycol-modified superoxide dismutase by chromatographic and electrophoretic techniques, JSnider et. al., Journal of Chromatography A 1992, 599, 141-155); but also bring some difficulties for the consistency between different batches of products and the validation of final product in drug synthesis; 2) linear PEG molecules has a high molecular weight, but can only connect the drug at both ends, inevitably resulting in decreased drug loading capacity.

In order to overcome the adverse effects of PEG, Dhawan et al. (Synthesis of polyamide oligomers based on 14-amino-3,6,9,12-tetraoxatetradecanoic acid, Dhawan et. al., Bioconjugate Chemistry 2000, 11, 14-21) prepared a linear discrete polyethylene glycol having the same structure with PEG (i.e., PEG with a defined molecular weight) and a derivative thereof by the reaction of sodium alkoxide with sulphonate in an organic synthesis process. The discrete polyethylene glycol has the same chemical formula as PEG, but the two are not identical, e.g., $PEG_{12}$ and $EG_{12}$ (dodecaethylene glycol), the former being a mixture of $EG_{11}$, $EG_{12}$, $EG_{13}$ and longer or shorter polyethylene glycol, and the latter being a definite compound containing only $EG_{12}$.

Although linear discrete polyethylene glycol solves the problem that PEG itself is not heterogeneous, it itself brings new problems. It preparation method requires protecting one end of the discrete polyethylene glycol at first and performing Williamson synthesis under strictly anhydrous conditions and then deprotecting to obtain discrete ethylene glycol with a longer chain segment. The synthesis method involves many steps, complicated operation and harsh conditions, requires strictly anhydrous conditions to get sodium alkoxide, and needs to use hydrogen for reduction in deprotection, which may limit its further spread and wide use, and although the loading capacity of polyethylene glycol with a relatively short chain segment has been improved, the water solubility is also significantly reduced, which may make its application range greatly limited.

In order to solve the drawbacks of the prior art, the present invention provides a Y-type discrete polyethylene glycol derivative and a preparation method thereof.

SUMMARY OF THE INVENTION

It is an object of the present invention to provide a Y-type discrete polyethylene glycol compound, which can solve the problem of heterogeneity of existing polyethylene glycol products and at the same time increase the drug loading capacity.

It is another object of the present invention to solve the problem of insufficient water solubility of the polyethylene glycol-modified insoluble drug caused by an increase of the loading capacity.

It is also an object of the present invention to provide a preparation method of the discrete polyethylene glycol compound, which involves simple steps, mild conditions, without need for strictly anhydrous environment or performing protection and deprotection steps.

Thus one aspect of the present invention is to provide a Y-type discrete polyethylene glycol derivative having the structure of formula (I):

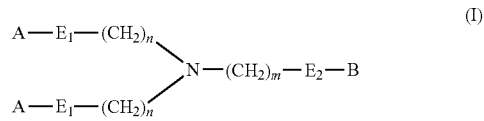

wherein:
m and n are integer of 0-30;
A and B are the same or different Y—X— structure;
X is a linking group selected from the group consisting of: —(CH$_2$)$_i$—, —(CH$_2$)$_i$NH—, —(CH$_2$)$_i$OCOO—, —(CH$_2$)$_i$OCONH—, —(CH$_2$)$_i$NHCONH—, —OC(CH$_2$)$_i$COO—, —(CH$_2$)$_i$COO— and —(CH$_2$)$_i$CONH—, i is an integer from 0 to 10;
Y is a reactive end group selected from the group consisting of C1-C6 alkoxy, hydroxy (—OH), amino (—NH$_2$), aminomethyl (—CH$_2$NH$_2$), maleimide

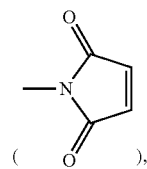

carboxy (—COOH), mercapto group (—SH), succinimide carbonate

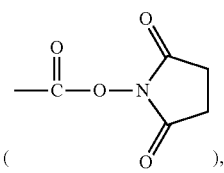

succinimide acetate

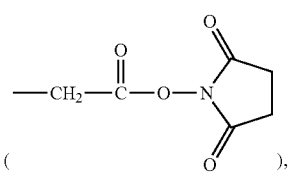

succinimide propionate

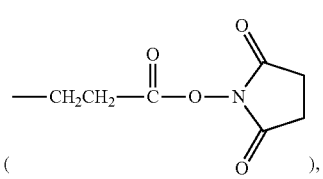

succinimide succinate

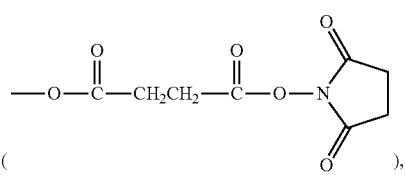

succinimide

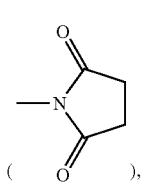

dithiopyridyl

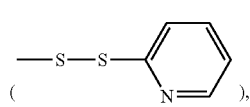

propionic acid (—CH$_2$CH$_2$COOH), aldehyde group (—CHO), thioester group

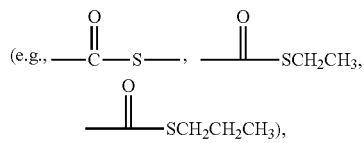

acryloxy

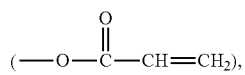

azido (—N$_3$), glutaric acid (e.g., —OCOCH$_2$CH$_2$CH$_2$COOH), hydrazide (—CONHNH$_2$), alkynyl (—C≡CH), p-nitrophenyl carbonate

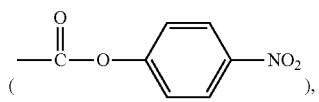

isocyanato (—NCO), silane (e.g., —Si(CH$_3$)$_3$, —Si(CH$_2$CH$_3$)$_3$, —Si(CH$_2$CH$_2$CH$_3$)$_3$), and carboxymethyl (—CH$_2$COOH);

E$_1$ is a discrete polyethylene glycol group with a structure of (CH$_2$CH$_2$O)$_j$, and j is an integer of 0 to 100;

E$_2$ is a discrete polyethylene glycol group with a structure of (CH$_2$CH$_2$O)$_k$, and k is an integer of 0 to 100.

Preferably, in the structure of formula (I) according to the present invention, m is an integer of 2 to 10, n is an integer of 2 to 10; more preferably, m is 2, 3, 4 or 5, and n is 2, 3, 4 or 5.

Preferably, in the structure of formula (I) according to the present invention, for the linking group X, i is an integer of 0 to 6, more preferably, i is 0, 1, 2, 3 or 4; and the linking group X is preferably —(CH$_2$)$_i$—, —(CH$_2$)$_i$NH— or (CH$_2$)$_i$CONH—.

Preferably, in the structure of formula (I) according to the present invention, the reactive group Y is selected from the group consisting of methoxy (—OCH$_3$), hydroxy, amino, mercapto group, carboxy, ester, aldehyde group, acryloxy or maleimide.

Preferably, in the structure of formula (I), for the discrete polyethylene glycol group E$_1$, j is an integer of 0 to 20, more preferably, j is an integer of 1 to 12, and most preferably j is 1, 2, 3, 4, 5, 6, 7 or 8.

Preferably, in the structure of formula (I), for the discrete polyethylene glycol group E$_2$, k is an integer of 0 to 20, more preferably, k is an integer of 1 to 12, and most preferably k is 1, 2, 3, 4, 5, 6, 7 or 8.

In one embodiment of the present invention, the Y-type discrete polyethylene glycol derivative has the following structure (II):

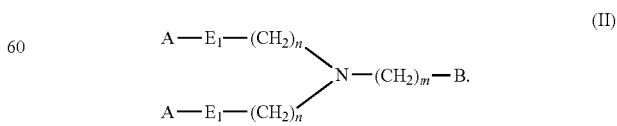

(II)

In one embodiment of the present invention, the Y-type discrete polyethylene glycol derivative has the following structure (III):

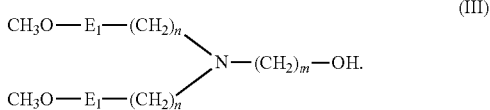

(III)

In one embodiment of the present invention, the Y-type discrete polyethylene glycol derivative has the following structure (IV):

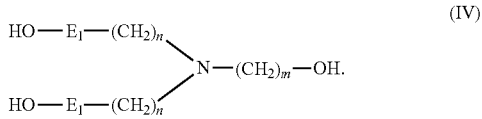

(IV)

In one embodiment of the present invention, the Y-type discrete polyethylene glycol derivative has the following structure (V):

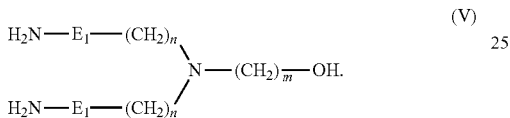

(V)

In one embodiment of the present invention, the Y-type discrete polyethylene glycol derivative has the following structure (VI):

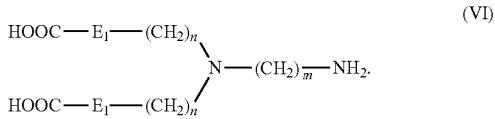

(VI)

In one embodiment of the present invention, the Y-type discrete polyethylene glycol derivative has the following structure (VII):

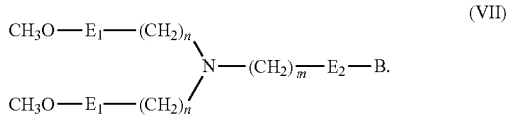

(VII)

In one embodiment of the present invention, the Y-type discrete polyethylene glycol derivative has the following structure (VIII):

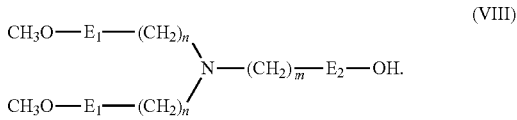

(VIII)

Another aspect of the present invention is to provide a preparation method of the Y-type discrete polyethylene glycol derivative of the formula (I), including the steps of:
(1) halogenating or sulfonating an end-group-modified discrete polyethylene glycol derivative, for example, methoxy discrete polyethylene glycol; (2) reacting the product of step (1) with a discrete polyethylene glycol derivative having an amino group at one end, and (3) optionally, modifying the end group of the product of step (2) to prepare the structure.

In the step (1) of the preparation method of the Y-type discrete polyethylene glycol derivative, the end-group-modified discrete polyethylene glycol derivative has a structure of Z—X-$E_1$-$(CH_2)_n$—OH,
wherein:
n is an integer of 0 to 30;
X is a linking group selected from the group consisting of: —$(CH_2)_i$—, —$(CH_2)_i$NH—, —$(CH_2)_i$OCOO—, —$(CH_2)_i$OCONH—, —$(CH_2)_i$NHCONH—, —OC$(CH_2)_i$COO—, —$(CH_2)_i$COO— and —$(CH_2)_i$CONH—, i is an integer from 0 to 10;
Z is a reactive end group defined by Y in the structure of formula (I) according to the present invention or Z is selected from the group consisting of methyl ester group (—COOCH$_3$), ethyl ester group (—COOCH$_2$CH$_3$), tert-butyl ester group (—COOC(CH$_3$)$_3$), aldehyde acetal group (e.g., —OCH(CH$_3$)$_2$, —OCH(CH$_2$CH$_3$)$_2$, —OCH(CH$_2$CH$_2$CH$_3$)$_2$), and benzyloxy ( 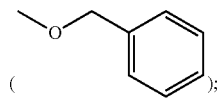 );

Y is: C1-C6 alkoxy, hydroxy, amino, aminomethyl, maleimide, carboxy, mercapto group, succinimide carbonate, succinimide acetate, succinimide propionate, succinimide succinate, succinimide, dithiopyridyl, propionic acid, aldehyde group, thioester group, acryloxy, azido, glutamic acid, hydrazide, alkynyl, p-nitrophenyl carbonate, isocyanato, silane, or carboxymethyl.

Preferably, said Z is methyl ester group, ethyl ester group, tert-butyl ester group, azido, aldehyde acetal group, or benzyloxy.

$E_1$ is a discrete polyethylene glycol group with a structure of $(CH_2CH_2O)_j$, and j is an integer of 0 to 100.

In a specific embodiment of the present invention, the step (1) may be carried out by adding methylene chloride (DCM) in a volume ratio of 1 to 100 times, preferably 1 to 20 times, more preferably 1 to 10 times, and triethylamine (TEA) at a molar ratio of 1 to 5 times, preferably 1 to 3 times, into an end-group-modified discrete polyethylene glycol derivative, then dissolving methanesulfonyl chloride (MsCl) or p-toluenesulfonyl chloride in a molar ratio of 1 to 3 times, preferably 1 to 2 times, in methylene chloride in a volume ratio of 1 to 30 times, preferably 1 to 20 times, more preferably 1 to 10 times, adding dropwise the both mixture to a reaction flask, reacting at room temperature for 1 to 48 hours, preferably 2 to 10 hours, washing the reaction solution with water 1 to 3 times, and evaporating the solvent to dryness to give the product, i.e., the sulfonylated product of the end-group-modified discrete polyglycol derivative.

Further, after the above steps, it is also included that: adding dimethylformamide (DMF) in a volume ratio of 1 to 100 times, preferably 1 to 20 times, more preferably 1 to 10 times, and lithium halide at a molar ratio of 1 to 5 times into a sulfonate derivative of the end-group-modified discrete polyglycol derivative, then heating to 30-80° C., reacting for 2 to 48 hours, preferably 2 to 10 hours, after the completion of the reaction, washing the organic phase with brine 1 to 3 times, evaporating the crude product to dryness and purifying by column chromatography to give the product, i.e., the halogenated product of the end-group-modified discrete polyglycol derivative. Preferably, said lithium halide is lithium bromide, and the halogenated product is a brominated product.

In a preferred embodiment of the present invention, the reaction for sulfonating an end-group-modified discrete polyethylene glycol derivative in the step (1) is shown as follows:

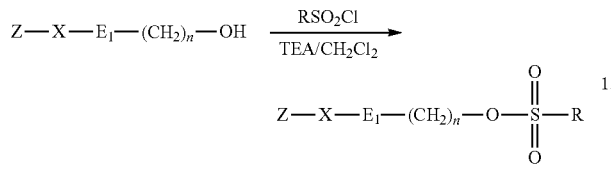

wherein said R is methyl or p-methylphenyl.

In the step (2) of the preparation method of the Y-type discrete polyethylene glycol derivative, the structural formula of the discrete polyethylene glycol derivative having an amino group at one end can be expressed as: $NH_2$—$(CH_2)_m$-$E_2$-X—Z;

wherein:

m is an integer of 0 to 30;

$E_2$ is a discrete polyethylene glycol group with a structure of $(CH_2CH_2O)_j$, and j is an integer of 0 to 100;

X is a linking group selected from the group consisting of: —$(CH_2)_i$—, —$(CH_2)_i$NH—, —$(CH_2)_i$OCOO—, —$(CH_2)_i$OCONH—, —$(CH_2)_i$NHCONH—, —OC$(CH_2)_i$COO—, —$(CH_2)_i$COO— and —$(CH_2)_i$CONH—, i is an integer from 0 to 10;

Z is a reactive end group defined by Y in the structure of formula (I) according to the present invention or Z is selected from the group consisting of methyl ester group, ethyl ester group, tert-butyl ester group, aldehyde acetal group, and benzyloxy.

Said Y is: C1-C6 alkoxy, hydroxy, amino, aminomethyl, maleimide, carboxy, mercapto group, succinimide carbonate, succinimide acetate, succinimide propionate, succinimide succinate, succinimide, dithiopyridyl, propionic acid, aldehyde group, thioester group, acryloxy, azido, glutamic acid, hydrazide, alkynyl, p-nitrophenyl carbonate, isocyanato, silane, or carboxymethyl.

Preferably, Z is methyl ester group, ethyl ester group, tert-butyl ester group, azido, aldehyde acetal group, or benzyloxy.

In a specific embodiment of the present invention, the step (2) of the preparation method of the Y-type discrete polyethylene glycol derivative comprises: adding the product of step (1) in a molar ratio of 1-5 times and tetrahydrofuran (THF) or N, N-dimethylformamide in a volume ratio of 1 to 100 times, preferably 1 to 20 times, more preferably 1 to 10 times, into the discrete polyethylene glycol derivative having an amino group at one end, reacting at 70-90° C. for 5 to 72 hours, preferably 2 to 10 hours, after evaporating the solvent to dryness, purifying the obtained crude product by column chromatography to obtain the product.

In a preferred embodiment of the present invention, the reaction of step (2) of the preparation method of the Y-type discrete polyethylene glycol derivative is shown as follows:

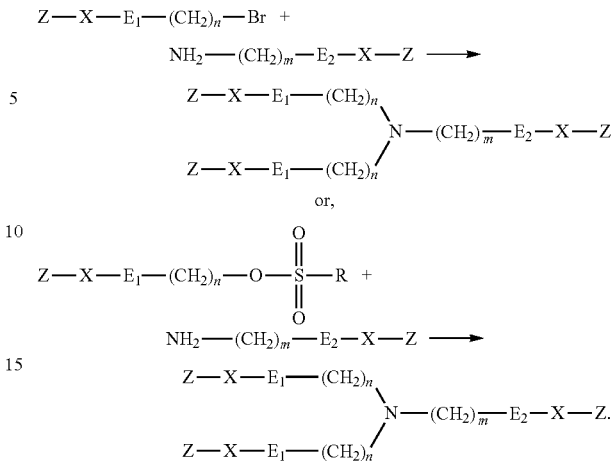

In another preferred embodiment of the present invention, the reaction of step (2) of the preparation method of the Y-type discrete polyethylene glycol derivative is shown as follows:

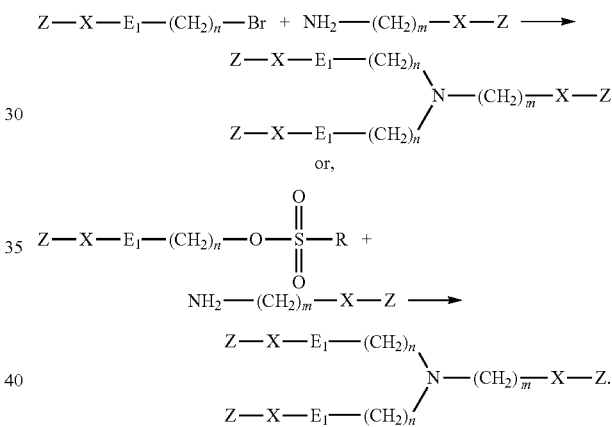

The step (3) of the preparation method of the present invention can be carried out according to the different groups of A or B in the Y-type discrete polyethylene glycol derivative to be prepared. Depending on the field and manner in which the Y-type discrete polyethylene glycol derivative is applied, it is sometimes necessary to modify the synthesized Y-type derivative, i.e., modify 1 to 3 end groups of the Y-type derivative to the desired reactive group(s). This modification can be carried out prior to said step (1): for example, first of all synthesizing a discrete polyethylene glycol derivative having an end group of a protected reactive group, methanesulfonylating, Y-typing and then deprotecting, to obtain a Y-type derivative with two end groups of reactive groups; or, first synthesizing a Y-type derivative and then modifying end group of A or B to obtain a Y-type derivative having an end group of a reactive group. It is also possible to apply both of the above-mentioned modes to obtain a Y-type derivative in which three end groups are modified. There are many specific modification ways, and a synthetic method which is readily available in the art can be used, such as carboxylation and subsequent succinimidation, amination, aldehyde-forming, thiolation, maleimidation, acrylation, and the like.

The Y-type discrete polyethylene glycol compound according to the present invention has the advantage of homogeneous molecular weight and high drug loading capacity, and after being linked to the insoluble drug molecule, the Y-type discrete polyethylene glycol compound according to the present invention can remarkably improve water solubility as compared with the drug molecule and the linear polyethylene glycol derivative of the drug molecule. In addition, the preparation method of the Y-type discrete polyethylene glycol compound of the present invention has simple steps and mild conditions, and is easy to be industrially operated.

DETAILED DESCRIPTION OF THE INVENTION

Example 1: Synthesis of $(mEG_3)_2N$—$C_3H_6$—OH

Figure 1:
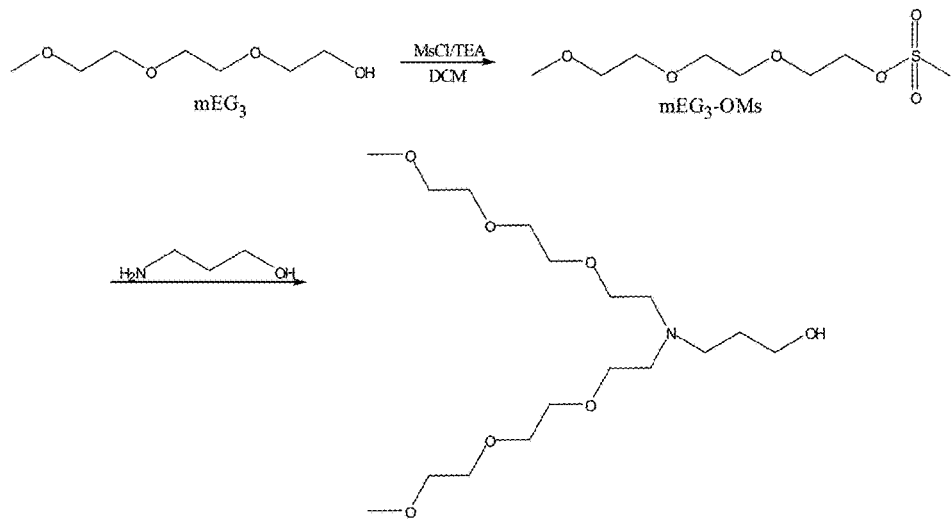
FIG. 1 is a synthetic route diagram of Y-type discrete polyethylene glycol derivative $(mEG_3)_2N$—$C_3H_6$—OH.

The synthetic route is shown in FIG. 1.

1. Synthesis of $mEG_3$-OMs

TEA (32 mL, 230 mmol) and 150 mL DCM were added to $mEG_3$-OH (32 mL, 200 mmol), and the resulting mixture was placed in a reaction flask in an ice-water bath. MsCl (17.5 mL, 220 mmol) was dissolved with DCM (50 mL), and when dissolved completely, the resulting mixture was dropwise added into the reaction flask in an ice-water bath. The reaction was carried out at room temperature for 3 hours. Whether the reaction was complete was detected by thin layer chromatography (TLC). The reaction mixture was washed three times with water (150 mL). The organic phase was dried over anhydrous sodium sulfate and the sodium sulfate was removed by filtration. About 52 g product was obtained after concentration.

2. Synthesis of Y—Type Small Molecule PEG $mEG_3$-OMs (21.6 g, 89.3 mmol) prepared in the above step 1 and THF (150 mL) were added into aminopropanol (3.1 g, 41.3 mmol). After heating and refluxing overnight, the supernatant solution was poured and evaporated to dryness to obtain a crude product, which was purified by a column (250 g silica gel, the mobile phase was MeOH/DCM system, MeOH/DCM=3-7%) to give the product in a yield of 2.5 g (16%).

NMR(CDCl$_3$) δ: 3.5-3.8 (m, 22H, OCH$_2$), 3.37 (s, 6H, CH$_3$O), 2.7-2.8 (m, 6H, N(CH$_2$)$_3$, 1.6-1.7 (m, 2H, NCH$_2$CH$_2$CH$_2$OH); ESI-MS: 368.3 (M+H)$^+$, 390.2 (M+Na)$^+$.

Example 2: Synthesis of $(mEG_5)_2N$—$C_3H_6$—OH

Figure 2:
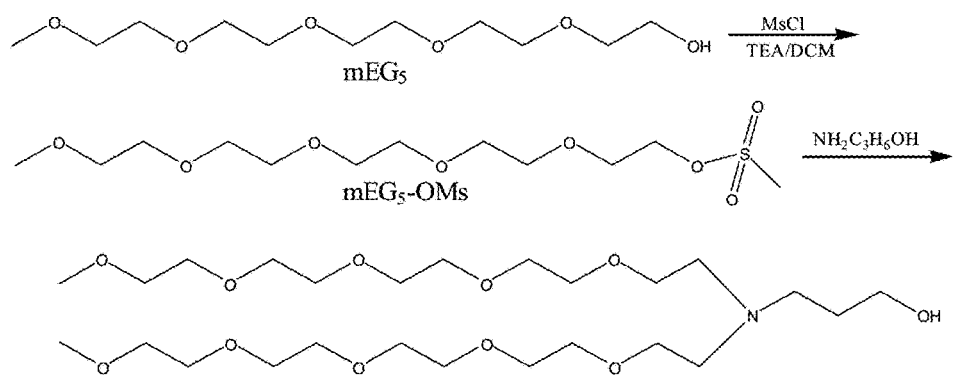
FIG. 2 is a synthetic route diagram of Y-type discrete polyethylene glycol derivative $(mEG_5)_2N$—$C_3H_6$—OH.

The synthetic route is shown in FIG. 2.

1. Synthesis of $mEG_5$-OMs

TEA (6.86 mL, 48 mmol) and DCM (60 mL) were added to $mEG_5$-OH (10.08 g, 40 mmol), and the resulting mixture was placed in a reaction flask in an ice-water bath. MsCl (3.56 mL, 46 mmol) was dissolved with DCM (40 mL), and the resulting mixture was dropwise added into the reaction flask in an ice-water bath. The reaction was carried out at room temperature for 3 hours. Whether the reaction was complete was detected by TLC. The reaction mixture was washed three times with water (150 mL). The organic phase was dried over anhydrous sodium sulfate and the sodium sulfate was removed by filtration. About 10 g product was obtained after concentration.

2. Synthesis of Y—Type Small Molecule PEG

Aminopropanol (0.45 g, 6.06 mmol), TEA (1 mL) and THF (100 mL) were added into the $mEG_5$-OMs (4 g, 12.1 mmol) prepared in the above step 1, after heating and refluxing overnight, the supernatant solution was poured and evaporated to dryness to obtain a crude product, which was purified by a column (the mobile phase was MeOH/DCM system, MeOH/DCM=3-7%) to give the product in a yield of 0.3 g (9.1%).

NMR(CDCl$_3$) δ: 3.5-3.8 (m, 38H, OCH$_2$), 3.37 (s, 6H, CH$_3$O), 2.7-2.8 (m, 6H, N(CH$_2$)$_3$, 1.6-1.7 (m, 2H, NCH$_2$CH$_2$CH$_2$OH); ESI-MS: 544.4 (M+H)$^+$, 566.3 (M+Na)$^+$.

Example 3: Synthesis of $(HO-EG_4)_2$-$C_3H_6$—OH

Figure 3:
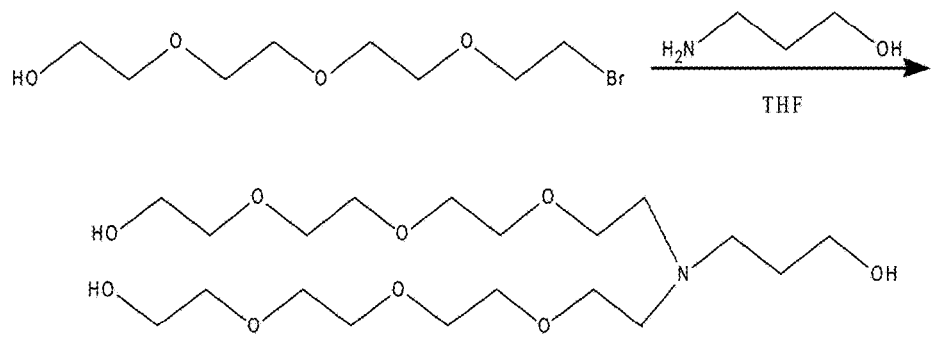
FIG. 3 is a synthetic route diagram of Y-type discrete polyethylene glycol derivative $(HO-EG_4)_2N$—$C_3H_6$—OH.

The synthetic route is shown in FIG. 3.

Aminopropanol (3.06 g, 40.9 mmol) and THF (150 mL) were added to HO-EG$_4$-Br (21 g, 81.7 mmol), after heating and refluxing overnight, the resulting mixture was cooled and evaporated to remove the solvent to obtain a crude product, which was purified by a column (the mobile phase was MeOH/DCM system, MeOH/DCM=0-10%) to give the product in a yield of 2.3 g (13.1%).

NMR(CDCl$_3$, hydrochloride) δ: 3.4-3.9 (m, 28H, —OCH$_2$—), 3.3 (m, 2H, —CH$_2$CH$_2$CH$_2$OH), 3.1-3.2 (m, 6H, —NCH$_2$—), 2.0 (m, 2H, —CH$_2$CH$_2$CH$_2$OH); ESI-MS: 428.4 (M+H)$^+$.

Example 4: Synthesis of $(NH_2-EG_4)_2N$—$C_3H_6$—OH

Figure 4:
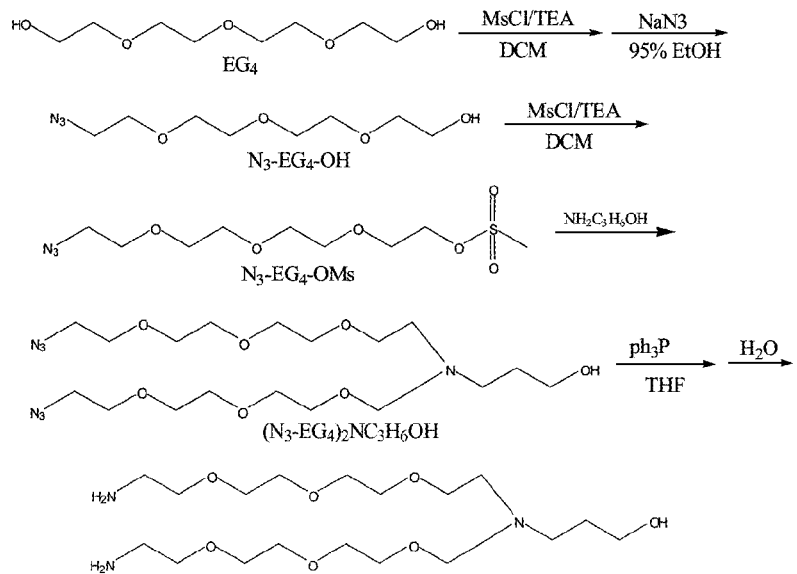
FIG. 4 is a synthetic route diagram of Y-type discrete polyethylene glycol derivative $(NH_2-EG_4)_2N$—$C_3H_6$—OH.

The synthetic route is shown in FIG. 4.

1. Synthesis of $N_3$-$EG_4$-OH

EG$_4$ (36 mL, 210 mmol), DCM (100 mL) and TEA (25 mL) were added to a reaction flask, which was placed in an ice-water bath. The resulting mixture was dropwise added with a DCM solution (100 mL) containing MsCl (5.81 mL, 75 mmol). The reaction was carried out at room temperature for 4 hours. The reaction mixture was washed once with water (100 mL) and evaporated to dryness to give a crude product.

95% ethanol (150 mL) and sodium azide (6.5 g, 100 mmol) were added to the crude product obtained in the previous step. The resulting mixture was refluxed at room temperature for 16 hours. The solid was removed by filtration, and the solution was evaporated to dryness. The substance obtained after evaporation was added with DCM (150 mL) and washed three times with water (100 mL). The DCM phase was evaporated to dryness to give 14 g crude product, which was purified by a column (250 g silica gel, the mobile phase was PE/EA system, PE/EA=50-0%) to give the product in a yield of 12.3 g (26.7%).

2. Synthesis of $N_3$-$EG_4$-OMs

TEA (8.6 mL, 60.3 mmol, 1.2 eq) and DCM (150 mL) were added into $N_3$-$EG_4$-OH (11 g, 50.2 mmol) prepared in the above step 1. The resulting mixture was placed in an ice-water bath. MsCl (4.5 mL, 57.8 mmol, 1.15 eq) was dissolved with DCM (50 mL), and the resulting mixture was added dropwise to the reaction flask in ice-water bath. The reaction was carried out overnight at room temperature. Whether the reaction was complete was detected by TLC. The reaction mixture was washed three times with water (100 mL). The organic phase was dried over anhydrous sodium sulfate and the sodium sulfate was removed by filtration. The product was obtained after concentration.

3. Synthesis of $(N_3-EG_4)_2N$—$C_3H_6$—OH

Aminopropanol (1.86 mL, 24.4 mmol) and DMF (130 mL) were added into $N_3$-$EG_4$-OMs (14.5 g, 48.8 mmol) prepared in the above step 2, after heating and refluxing overnight, the resulting mixture was evaporated to dryness to obtain a crude product, which was purified by a column (the mobile phase was MeOH/DCM system, MeOH/DCM=3-7%) to give the product in a yield of 1.2 g (10.3%).

4. Synthesis of $(NH_2-EG_4)_2N$—$C_3H_6$—OH

DMF (20 mL) and triphenylphosphine (615 mg, 2.35 mmol, 1.4 eq*2) were added to $(N_3-EG_4)_2N$—OH (400 mg, 0.84 mmol) prepared in the above step 3, and after reacting overnight at room temperature, the resulting mixture was added with water (0.1 mL), then the reaction was carried out overnight. The resulting mixture was evaporated to remove DMF, added with water (50 mL), successively washed twice with toluene (40 mL) and DCM (30 mL), and evaporated to remove moisture to give the product in a yield of 300 mg (84%).

NMR ($D_2O$) δ: 3.5-3.8 (m, 38H, $OCH_2$), 2.4-2.8 (m, 10H, $N(CH_2)_3$ 及 $NH_2CH_2$, 1.6-1.7 (m, 2H, $NCH_2CH_2CH_2OH$); ESI-MS: 448.4 $(M+Na)^+$.

Example 5: Synthesis of $(HOOC-EG_4)_2N$—$C_2H_4$—$NH_2$

Figure 5:
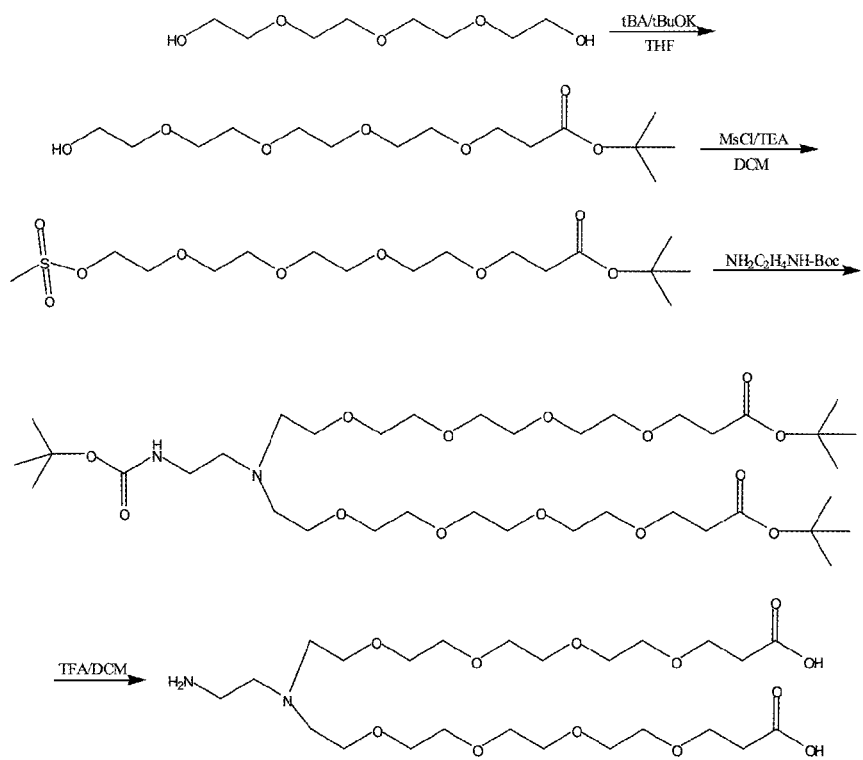
FIG. 5 is a synthetic route diagram of Y-type discrete polyethylene glycol derivative $(HOOC-EG_4)_2N$—$C_2H_4$—$NH_2$.
Figure 6:
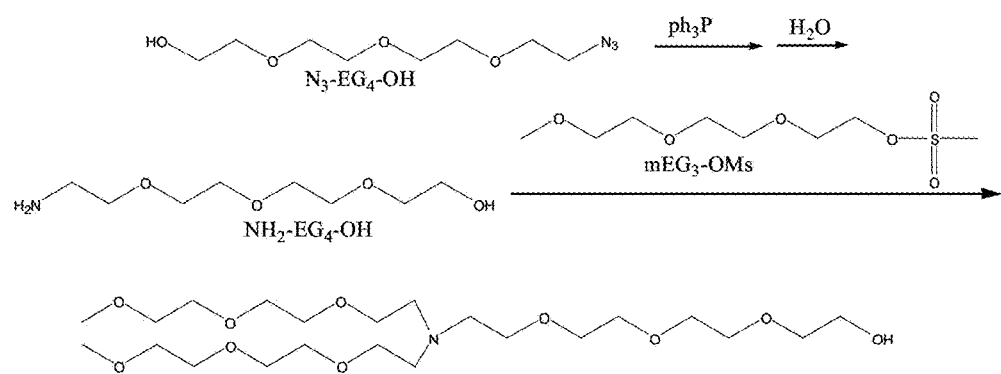
FIG. 6 is a synthetic route diagram of Y-type discrete polyethylene glycol derivative $(mEG_3)_2N$-$EG_4$-OH.

The synthetic route is shown in FIG. 5.

1. Synthesis of MsO-$EG_4$-OtBu

DCM (350 mL) and TEA (22.7 mL, 0.159 mol, 1.3 eq) were added to HO-$EG_4$-tBu (39.4 g, 0.122 mol). The resulting mixture was added with a solution of MsCl (11.4 mL, 0.146 mol, 1.2 eq) in DCM (150 mL) under ice-water bath. The reaction was carried out overnight at room temperature. The resulting mixture was successively washed with water (200 mL) three times, dried over anhydrous sodium sulfate, filtered and evaporated to remove the solvent to give the product.

2. Synthesis of $(tBuO-EG_4)_2N$—$C_2H_4$—NH-Boc $NH_2$—$C_2H_4$—NH-Boc (4 g, 25 mmol) and THF (200 mL) were added to tBu-$EG_4$-OMs (20 g, 50 mmol) prepared in the above step 1, the resulting mixture was stirred overnight at room temperature and concentrated to obtain a crude product, which was purified by a column (MeOH/DCM=0-10%) to give the product in a yield of 2.3 g (12.0%).

3. Synthesis of $(HOOC-EG_4)_2N$—$C_2H_4$—$NH_2$

DCM (20 mL) and trifluoroacetic acid (TFA) (8 mL) were added into $(tBuO-EG_4)_2N$—$C_2H_6$—NH-Boc (2.3 g, 3.0 mmol) prepared in the above step 2. The reaction was carried out overnight at room temperature. The resulting mixture was evaporated to remove the solvent to obtain the product in a yield of 2.2 g (94.0%). NMR($CDCl_3$) δ: 2.6-2.7 (t, 4H, $CH_2COO$); 3.5-3.8 (m, 40H, other hydrogen); ESI-MS: 557.4 $(M+H)^+$, 595.3 $(M+Na)^+$.

Example 6: Synthesis of $(mEG_3)_2N$-$EG_4$-OH

1. Synthesis of $NH_2$-$EG_4$-OH

THF (50 mL) was added to $N_3$-$EG_4$-OH (9.2 g, 42.0 mmol). The resulting mixture was placed in an ice-water bath, and added dropwise with THF (75 mL) containing triphenylphosphine (13.21 g, 50.4 mmol, 1.2 eq). The reaction was carried out at room temperature for 24 hours. The resulting mixture was added with water (1965 uL, 109.2 mmol, 2.6 eq), and reacted at room temperature overnight. The resulting mixture was evaporated to remove the solvent, added with water (150 mL), washed with toluene (150 mL) and DCM (100 mL), and evaporated to remove the water phase to give 8 g product.

2. Synthesis of $(mEG_3)_2N$-$EG_4$-OH $NH_2$-$EG_4$-OH (4.3 g, 22.3 mmol) prepared in step 1 and THF (150 mL) were added to $EG_3$-OMs (10.8 g, 44.6 mmol). The resulting mixture was refluxed and stirred overnight, and evaporated to remove the solvent to obtain a crude product, which was purified by a column (the mobile phase was MeOH/DCM system, MeOH/DCM=3-7%) to give the product in a yield of 2.1 g (19.4%). NMR($CDCl_3$) δ: 3.5-3.8 (m, 34H, $OCH_2$), 3.37 (s, 6H, $CH_3O$), 2.7-2.8 (m, 6H, $N(CH_2)_3$; ESI-MS: 486.4 $(M+H)^+$, 508.4 $(M+Na)^+$.

Example 7: Synthesis of Cholesterol Derivative of $(mEG_3)_2N$—$C_3H_6$—OH

DCM (20 mL) and TEA (0.905 mL, 6.53 mmol) were added to the $(mEG_3)_2N$—$C_3H_6$—OH (2 g, 5.45 mmol) prepared in Example 1. The cholesterol chloroformate (2.57 g, 5.72 mmol) was dissolved in DCM (30 mL), and the resulting mixture was added dropwise to the reaction flask. The resulting mixture was stirred overnight at room temperature. Whether the reaction was complete was detected by TLC. The resulting mixture was washed once with water, and spin-dried to obtain a crude product, which was purified by a column (the mobile phase was MeOH/DCM system, MeOH/DCM=0-7%) to give 1.4 g product (32.4%).

NMR($CDCl_3$) δ: 5.55-5.45 (m, 1H), 4.65-4.50 (m, 1H), 4.1-4.0 (m, 2H), 3.5-3.8 (m, 20H), 3.37 (s, 6H), 2.7-2.8 (m, 6H), 2.50-0.80 (m, 42H), 0.65-0.60 (m, 3H).

Example 8: Synthesis of Cholesterol Derivative of $mEG_7$-OH

A cholesterol derivative of $mEG_7$-OH was prepared under the same conditions as in Example 7 by commercially available $mEG_7$-OH.

NMR($CDCl_3$) δ: 5.55-5.45 (m, 1H), 4.65-4.50 (m, 1H), 4.1-4.0 (m, 2H), 3.5-3.8 (m, 26H), 3.37 (s, 3H), 2.50-0.80 (m, 40H), 0.65-0.60 (m, 3H).

Figure 7:
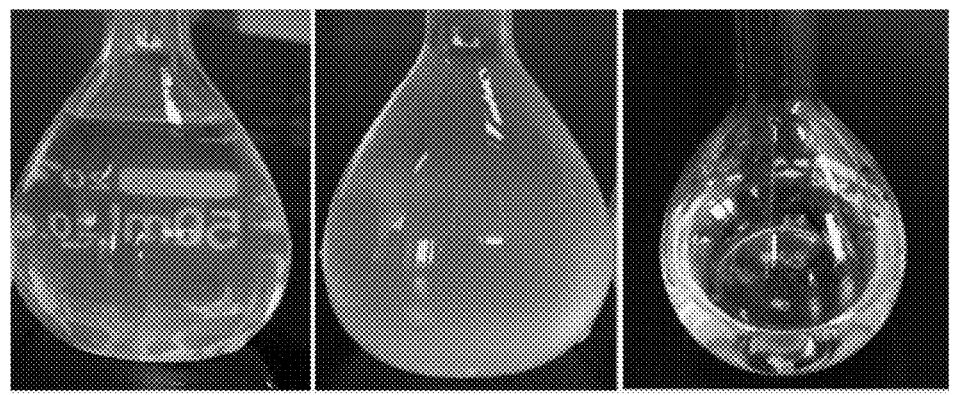
FIG. 7 shows the results of a dispersibility comparison test of cholesterol and cholesterol derivatives in aqueous solution (from the left to the right are the aqueous solutions of cholesterol derivative of $(mEG_3)_2N$—$C_3H_6$—OH, cholesterol derivative of $mEG_7$-OH and cholesterol with the same concentration, respectively.)

Example 9: Comparison Test of Dispersion of Cholesterol and Cholesterol Derivatives in Water 20 mg cholesterol derivative of $(mEG_3)_2N$—$C_3H_6$—OH prepared in Example 7, 20 mg cholesterol derivative of $mEG_7$-OH prepared in Example 8 and 20 mg cholesterol were placed in a 50 mL volumetric flask, which was added with water to the scale, and placed in 20° C. water bath, shaken vigorously every 5 min for 30 min. After 30 min, the dispersion of the two cholesterol derivatives and cholesterol in water were shown in FIG. 7, from the left to the right are successively cholesterol derivative of $(mEG_3)_2N$—$C_3H_6$—OH, cholesterol derivative of $mEG_7$-OH and cholesterol. The results with the naked eye observation showed that the dispersion liquid of cholesterol derivative of $(mEG_3)_2N$—$C_3H_6$—OH was translucent light blue, and the handwriting behind the volumetric flask can be clearly seen; and the cholesterol derivative of $mEG_7$-OH was a white emulsion, and cholesterol is completely insoluble.

Example 10: Comparison Test of Solubility of Cholesterol Derivatives in Water

The solubility of cholesterol derivatives in water was determined according to the method in "Chinese pharmacopoeia":

21.3 mg cholesterol derivative of $(mEG_3)_2N$—$C_3H_6$—OH prepared in Example 7 was dispersed in 50 mL water. 5 mL was taken out therefrom, and added with 1.5 mL water, the resulting mixture was placed in a 20° C. water bath, and shaken vigorously every 5 min for 30 min. After 30 min, 1.5 mL water was further added, and the resulting mixture was placed in a 20° C. water bath with the same procedure for dissolution. Until 9 mL water was added, the solution was clear.

24.2 mg cholesterol derivative of $mEG_7$-OH prepared in Example 8 was dispersed in 50 mL water. 5 mL was taken out therefrom, and added with 5 mL water, the resulting mixture was placed in a 20° C. water bath, and shaken vigorously every 5 min for 30 min. After 30 min, 5 mL water was further added, and the resulting mixture was placed in a 20° C. water bath with the same procedure for dissolution until 25 mL water was added. 5 mL solution was taken from the dilute solution, the same procedure was carried out until 10 mL water was added, and the solution was clear.

From the results analysis, it was found that the solubility of cholesterol derivative of $(mEG_3)_2N$—$C_3H_6$—OH was 15.2 mg/100 g, which was 3.3 times the solubility of cholesterol derivative of $mEG_7$-OH, 4.61 mg/100 g, and was 76 times the solubility of cholesterol (<0.2 mg/100 g).

The invention claimed is:

1. A Y-type discrete polyethylene glycol derivative having the structure of formula (I):

$$A\text{—}E_1\text{—}(CH_2)_n\diagdown N\text{—}(CH_2)_{\overline{m}}\text{—}E_2\text{—}B$$
$$A\text{—}E_1\text{—}(CH_2)_n\diagup$$
(I)

wherein:
in and n are integer of 0-30;
A and B are the same or different Y—X— structure;
X is a linking group selected from the group consisting of:
—$(CH_2)_i$—, —$(CH_2)_iNH$—, —$(CH_2)_iOCOO$—, —$(CH_2)_iOCONH$—, —$(CH_2)_iNHCONH$—, —OC$(CH_2)_iCOO$—, —$(CH_2)_iCOO$— and —$(CH_2)_i$CONH—, i is an integer from 0 to 10;

Y is a reactive end group selected from the group consisting of C1-C6 alkoxy, hydroxy, amino, aminomethyl, maleimide, carboxy, mercapto group, succinimide carbonate, succinimide acetate, succinimide propionate, succinimide succinate, succinimide, dithiopyridyl, propionic acid, aldehyde group, thioester group, acryloxy, azido, glutaric acid, hydrazide, alkynyl, p-nitrophenyl carbonate, isocyanato, silane, and carboxymethyl;

$E_1$ is a discrete polyethylene glycol group with a structure of $(CH_2CH_2O)_j$, and j is an integer of 1 to 100;

and, $E_2$ is a discrete polyethylene glycol group with a structure of $(CH_2CH_2O)_k$, and k is an integer of 1 to 100.

2. The Y-type discrete polyethylene glycol derivative of claim 1, wherein in is an integer of 2 to 10, and/or, n is an integer of 2 to 10.

3. The Y-type discrete polyethylene glycol derivative of claim 2, wherein in is 2, 3, 4 or 5, and/or, n is 2, 3, 4 or 5.

4. The Y-type discrete polyethylene glycol derivative of claim 1, wherein the linking group X is —$(CH_2)_i$—, —$(CH_2)_iNH$— or $(CH_2)_i$CONH—.

5. The Y-type discrete polyethylene glycol derivative of claim 1, wherein for the linking group X, i is 0, 1, 2, 3 or 4.

6. The Y-type discrete polyethylene glycol derivative of claim 1, wherein the reactive group Y is selected from the group consisting of methoxy, hydroxy, amino, mercapto, carboxy, ester, aldehyde group, acrylic or maleimide.

7. The Y-type discrete polyethylene glycol derivative of claim 1, wherein for the discrete polyethylene glycol group $E_1$, j is an integer of 1 to 20; and/or,
for the discrete polyethylene glycol group $E_2$, k is an integer of 1 to 20.

8. The Y-type discrete polyethylene glycol derivative of claim 7, wherein j is an integer of 1 to 12, and/or, k is an integer of 1 to 12.

9. The Y-type discrete polyethylene glycol derivative of claim 8, wherein j is 1, 2, 3, 4, 5, 6, 7 or 8; and/or, k is 1, 2, 3, 4, 5, 6, 7 or 8.

10. The Y-type discrete polyethylene glycol derivative of claim 1, wherein the Y-type discrete polyethylene glycol derivative has the following structure:

$$CH_3O\text{—}E_1\text{—}(CH_2)_n\diagdown N\text{—}(CH_2)_{\overline{m}}\text{—}E_2\text{—}OH.$$
$$CH_3O\text{—}E_1\text{—}(CH_2)_n\diagup$$
(VIII)

11. The Y-type discrete polyethylene glycol derivative of claim 1, wherein
the Y-type discrete polyethylene glycol derivative has the following structure with a structure of:

* * * * *